(12) United States Patent
Barker

(10) Patent No.: US 10,084,274 B2
(45) Date of Patent: Sep. 25, 2018

(54) UNIVERSAL ADAPTOR FOR DEFIBRILLATORS AND/OR ELECTROCARDIOGRAMS AND METHODS ASSOCIATED THEREWITH

(71) Applicant: Roman Hayden Barker, Winston Salem, NC (US)

(72) Inventor: Roman Hayden Barker, Winston Salem, NC (US)

( * ) Notice: Subject to any disclaimer, the term of this patent is extended or adjusted under 35 U.S.C. 154(b) by 0 days.

(21) Appl. No.: 14/813,150

(22) Filed: Jul. 30, 2015

(65) Prior Publication Data

US 2017/0027471 A1 Feb. 2, 2017

(51) Int. Cl.
*A61B 5/0428* (2006.01)
*A61N 1/04* (2006.01)
*H01R 31/06* (2006.01)
*A61B 5/0408* (2006.01)

(52) U.S. Cl.
CPC ......... *H01R 31/06* (2013.01); *A61B 5/04288* (2013.01); *A61N 1/046* (2013.01); *A61N 1/048* (2013.01); *A61B 2562/227* (2013.01)

(58) Field of Classification Search
None
See application file for complete search history.

(56) References Cited

U.S. PATENT DOCUMENTS

| | | | | |
|---|---|---|---|---|
| 4,746,298 A * | 5/1988 | Hollander | ............... | H01R 27/00 439/222 |
| 5,176,543 A * | 1/1993 | Brooks | ................... | A61N 1/048 439/859 |
| 5,341,812 A * | 8/1994 | Allaire | ............... | A61B 5/04286 600/508 |
| 5,660,554 A * | 8/1997 | Mead | ..................... | H01R 27/00 439/172 |
| 5,679,022 A * | 10/1997 | Cappa | ...................... | A61N 1/05 439/502 |
| 5,782,892 A * | 7/1998 | Castle | .................. | A61N 1/3752 439/909 |
| 5,931,304 A * | 8/1999 | Hammond | .............. | A61F 17/00 206/425 |
| 6,152,778 A * | 11/2000 | Dalton | ................... | H01R 31/06 439/502 |
| 7,277,752 B2 * | 10/2007 | Matos | .................. | A61B 5/0006 600/509 |
| 7,444,177 B2 * | 10/2008 | Nazeri | ................. | A61B 5/0006 600/382 |
| 7,465,187 B1 * | 12/2008 | Wu | ........................ | H01R 31/02 439/502 |
| 8,613,627 B2 * | 12/2013 | Selig | .................. | A61B 18/1206 439/222 |
| 8,668,651 B2 * | 3/2014 | Burnes | ............... | A61B 5/04286 600/372 |

(Continued)

*Primary Examiner* — Brian T Gedeon
(74) *Attorney, Agent, or Firm* — Ben Schroeder Law PLLC

(57) ABSTRACT

The present invention relates to a universal adaptor that allows one to connect electrodes and/or electrode pads from a patient that is experiencing heart problems to an EKG and/or defibrillator from a different manufacturer from the manufacturer of the electrodes and/or electrode pads. The invention also relates to methods of saving a patient's life by eliminating the process and time that it would take to transfer electrodes and/or electrode pads on a patient by using this universal adaptor.

20 Claims, 4 Drawing Sheets

(56) References Cited

U.S. PATENT DOCUMENTS

| | | | |
|---|---|---|---|
| 8,753,149 B2* | 6/2014 | Lee | H01R 13/4534 |
| | | | 439/653 |
| 9,072,444 B2* | 7/2015 | Burnes | A61B 5/04286 |
| D741,265 S * | 10/2015 | Lee | D13/137.2 |
| 9,204,794 B2* | 12/2015 | Lisogurski | A61B 5/00 |
| 9,226,678 B1* | 1/2016 | Ghaffari | A61B 5/0408 |
| 2002/0115912 A1* | 8/2002 | Muraki | A61B 5/02055 |
| | | | 600/300 |
| 2007/0191789 A1* | 8/2007 | Hickle | A61M 5/172 |
| | | | 604/257 |
| 2012/0089369 A1* | 4/2012 | Abuzeni | H04L 67/12 |
| | | | 702/188 |

\* cited by examiner

UNIVERSAL ADAPTOR FOR DEFIBRILLATORS AND/OR ELECTROCARDIOGRAMS AND METHODS ASSOCIATED THEREWITH

FIELD OF THE INVENTION

The present invention relates to a universal adaptor for defibrillators and electrocardiograms that allows a plurality of different defibrillators and electrocardiograms to be attached to electrodes and/or leads to patients. The present invention also relates to methods of saving a person's life who has undergone or may be likely to undergo a heart attack wherein the method employs the universal adaptor of the present invention.

BACKGROUND OF THE INVENTION

Cardiovascular diseases claim more lives than all forms of cancer combined. Heart disease (which includes Heart Disease, Stroke and other Cardiovascular Diseases) is the No. 1 cause of death in the United States, killing between 600,000 and 800,000 every year. Heart disease affects men and women almost equally and is the leading cause of death for people of most racial/ethnic groups in the United States, including African Americans, Hispanics and Whites. For Asian Americans or Pacific islanders and American Indians or Alaska Natives, heart disease is second only to cancer.

In the United States, someone has a heart attack, every 34 seconds. Every 60 seconds, someone in the United States dies from a heart disease-related event. About 720,000 people in the U.S. suffer heart attacks each year. Of these, 515,000 are a first heart attack and 205,000 happen in people who have already had a heart attack.

In 2011, about 326,200 people experienced out-of-hospital cardiac arrests in the United States. Of those treated by emergency medical services, 10.6 percent survived. Of the 19,300 bystander-witnessed out-of-hospital cardiac arrests in die same year, 31.4 percent survived.

Moreover, every year about 735,000 Americans have a heart attack. Of these, 525,000 are a first heart attack and 210,000 happen in people who have already had a heart attack. Morbidity and mortality from myocardial infarction are significantly reduced if patients and bystanders recognize symptoms early, activate the emergency medical service (EMS) system, and thereby shorten the time to definitive and continuous treatment. Trained prehospital personnel can provide life-saving interventions if the patient develops cardiac arrest. The key to improved survival is the availability and use (if necessary) of early defibrillation. Approximately 1 in every 300 patients with chest, pain transported to the ED by private vehicle goes into cardiac arrest en route.

For anyone having an MI (myocardial infarction), getting rapid medical attention is absolutely critical for two reasons: Most of the cardiac arrests seen with acute MIs occur within the first few hours. If the cardiac arrest happens after you have come under adequate medical care, there is an excellent chance it can be successfully treated; otherwise the odds of surviving a cardiac arrest are very low.

Both the short-terra and the long-term consequences of an MI are largely determined by how much of your heart muscle dies. With rapid and aggressive medical treatment, the blocked artery can usually be opened quickly, thus preserving most of the heart muscle that is at risk of dying. If treatment is given within three or four hours, much of the permanent muscle damage can be avoided. But if treatment is delayed beyond five or six hours, the amount of heart muscle that can be saved drops off significantly. After about 12 hours, the damage is usually irreversible.

Getting rapid and appropriate medical care requires that several things occur. First, it requires that one knows the signs of a heart attack, and seeks medical help the moment one thinks one might be having a heart attack. Second, it requires that the medical personnel who are caring for you do the right things, and do them quickly. Third, medical care must be adequate and continuous until the danger from the heart attack subsides.

The use of an automated external defibrillator (AED) on a person who is having sudden cardiac arrest (SCA) may save the person's life. The most common cause of SCA is art arrhythmia called ventricular fibrillation wherein the ventricles don't beat normally. Rather, the ventricles quiver very rapidly and irregularly. Another arrhythmia that may lead to SCA is ventricular tachycardia wherein a fast, regular beating of the ventricles may last for a few seconds or much longer. In people who have either of these arrhythmias, an electric shock from an AED can restore the heart's normal rhythm (if done within minutes of the onset of SCA). The patient should be continuously monitored before during and after these events in case additional shock is needed.

In some circumstances, if an individual is having a SCA, the individual may suddenly collapse and lose consciousness. Alternatively and/or additionally, the person may be unconscious and unable to respond when called or shaken. The person may not be breathing, or they may have an abnormal breathing pattern. Generally, a pulse may not be present. Moreover, the person's skin may acquire a dark or blue tint from lack of oxygen. Also, the person, may not move, or his or her movements may look like a seizure (spasms).

Rapidly applying electrodes and leads to a potential SCA individual and using an AED will allow emergency medical personnel to check the person's heart rhythm and determine whether an electric shock is needed to try to restore a normal rhythm. The electronic shock may in some cases be applied by emergency medical technicians (EMTs) prior to heading to, or alternatively, on the way to an emergency medical care facility (e.g., a hospital). Additionally and/or alternatively, a shock may be applied once the patient has arrived at the emergency care facility. However, one problem that may occur is if the emergency medical care facility has different EKG machines and/or different defibrillators from the EMTs that transfer the patient to the hospital. This will often require the removal of electrodes and/or leads and from the patient and having new ones employed. The removal and re-applying of electrodes adds time to a patient's care in which time is of the essence. A failure to adapt the patient quickly to different machines may prove to be fatal. The present invention has been developed with these shortcomings in mind.

BRIEF SUMMARY OF THE INVENTION

The present invention relates to a universal adaptor for defibrillators and electrocardiograms that allow a plurality of different defibrillators and electrocardiograms to be attached to electrodes and/or leads that are attached to patients. The present invention also relates to methods of saving a person's life who has undergone or may be likely to undergo a heart attack wherein the method, employs the universal adaptor of the present invention.

DETAILED DESCRIPTION OF THE INVENTION

Figure 1:
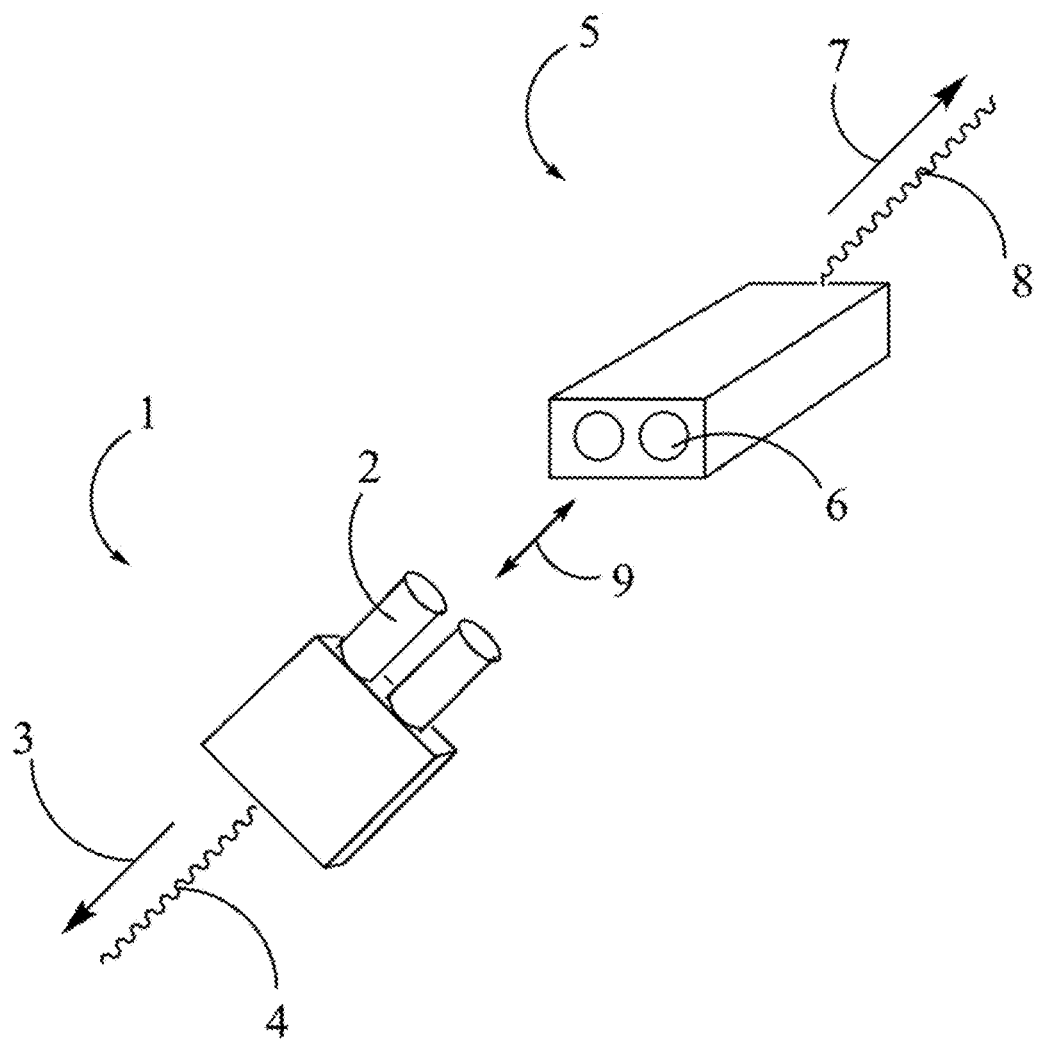
FIG. 1 shows a plug portion and a corresponding plug receiving portion for an embodiment that does not require a universal adaptor.

The present invention relates to a universal adaptor for defibrillators and electrocardiograms that allows a plurality of different defibrillators and electrocardiograms to be attached to electrodes and/or leads that are attached to patients. The present invention also relates to methods of saving a person's life who has undergone or may be likely to undergo a heart attack wherein the method employs the universal adaptor of the present invention.

A plurality of EKG manufacturers exist and these include Bionet, Brentwood Midmark, Burdick, Cardioline, Datex Ohmeda, Dr. Lee, Fukuda Denshi, General Electric, Hewlett Packard, Medtronic, Mortara, Nihon Kohden, Philips, QRS, Ritter, Schiller, and Welch Allyn.

A plurality of defibrillators exist and these include machines made by Cardiac Science, Defibtech, HeartSine Technologies, Inc., Laerdal Medical Corporation, Medical Research Laboratories, Inc., Medtronic Physio-Control Corporation, Philips Medical Systems/Heartstream, Physio-Control, and ZOLL Medical Corporation.

In one embodiment, the present invention relates to products and methods allowing any of a plurality of electrodes/leads to be connected to any of a plurality of defibrillator/EKG machines. To illustrate one embodiment of the invention, an exemplary scenario with a heart attack victim is described.

An individual (e.g. a patient) may call EMTs because the patient is exhibiting symptoms that make the patient think that he/she may be having a heart attack. The EMTs rush to the scene where the patient is. The EMTs do a quick evaluation of the patient and realize that they should place electrodes/electrode pads on the patient's chest. The electrode pads packaging is opened, the backing to the electrode pads are removed, and the electrodes/electrode pads are placed on the patient's chest. In a variation, the electrode/electrode pads have leads attached to them which connects the electrode/electrode pads to a plug portion. In an embodiment, the plug portion is connected to a corresponding plug receiving portion, which is attached to a lead/wire which is attached to an EKG machine and/or a defibrillator.

In an embodiment, the patient may be connected to an EKG, which may not have the capability to deliver a shock that traditionally is delivered by a defibrillator. The EKG may indicate that a shock is warranted. Rather than removing the electrode pads from the patient to administer the shock, one may simply unplug the plug portion from the corresponding plug receiving portion that is attached to the EKG, use the universal adaptor and connect the electrodes/electrode pads via the plug portion to a corresponding plug receiving portion that is attached via wires to a defibrillator and administer the requisite shock. The patient may then be transported via ambulance to a hospital. In an embodiment, the EMTs' EKG and/or defibrillator may be entirely inconsistent with the EKGs/defibrillators at the hospital such that the electrodes/electrode pads that have been placed on the patient may not be easily adapted to be connected to the hospital's EKG/defibrillator machines. However, with a universal adaptor, the plug portion from the EMTs' electrodes/electrode pads can be connected to a corresponding plug receiving portion that is connected to the hospital's EKG/defibrillator machine(s), allowing the EMTs' electrodes/electrode pads to be connected to the hospital's EKG/defibrillator machine(s).

In an embodiment, the present invention relates to an electrode unit, which in one variation, includes an electrode pad and an electrode connector. The electrode pad is generally made of a conductive material and is adhered to a patient during a medical procedure. The electrode connector connects the electrode pad to a medical device, such as a defibrillator or an EKG machine. In a variation, the electrode connector includes lead wires which electrically connect the electrode pad to a plug portion. Additionally, in certain embodiments, a conductive gel at least partially covers the electrode pad and is protected by a cover. The cover may be any suitable sheet which is capable of adhering to the electrode pad via a conductive gel. One possible sheet material is silicone-coated mylar. Other materials are contemplated and therefore within the scope of the present invention.

In general, the conductive pad may not be compatible with a particular defibrillator because the plug portion of the conductive pad is not compatible with the corresponding plug receiving portion that is connected to the EKG or defibrillator. Thus, in one embodiment of the invention, a universal adaptor can be employed, which is able to adapt the plug portion of the conductive pad so that it can be used with the corresponding plug receiving portion of any of a plurality of defibrillators/EKGs. In an embodiment, a user can tear the electrode package open to expose its contents, which may contain not only a plug portion but a universal adaptor, which can allow the electrodes/electrode pads to be connected to almost any existing EKG/defibrillator machine(s).

The invention will now be described in connection with the figures. FIG. 1 shows a plug portion 1 and a corresponding plug receiving portion 5 for an embodiment that does not require a universal adaptor. The cylindrical male prongs 2 are designed so as to fit into cylindrical female receptors 6. The lead/wire 4 goes in the direction of arrow 3 to the electrodes/electrode pads (not shown) and the lead wire 8 goes in the direction of arrow 7 to the EKG and/or defibrillator machine(s) (not shown). When plug portion 1 is inserted into corresponding plug receiving portion 5 (as shown by double arrow 9), the patient is connected via electrodes/electrode pads through the plug portion 1 and the corresponding plug receiving portion 5 to the EKG/defibrillator machine(s) so as to allow the patient to be monitored and/or a requisite shock delivered.

Figure 2:
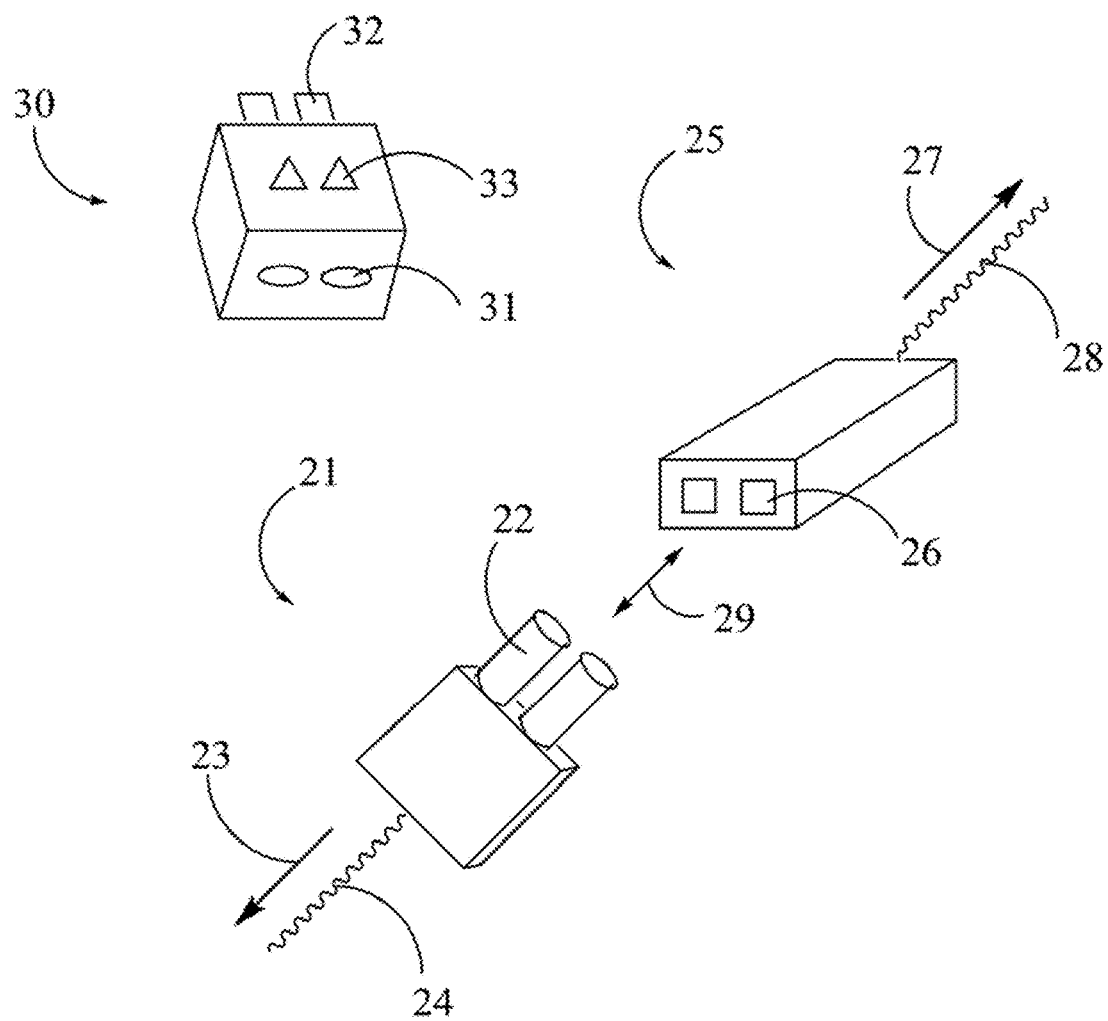
FIG. 2 shows a universal adaptor and a plug portion and a corresponding plug receiving portion for an embodiment that requires a universal adaptor.

FIG. 2 shows an embodiment of the invention wherein the plug portion 21 and a corresponding plug receiving portion 25 requires a universal adaptor 30. As shown in FIG. 2, the cylindrical male prongs 22 of the plug portion 21 is not designed to fit into rectangular female receptors 26 of the corresponding plug receiving portion 25. Accordingly, connection cannot be easily made between the electrodes/electrode pads which are present on the patient at the end of lead 24 in the direction of arrow 23 and the EKG/defibrillator machine(s) which is present at the end of lead 28 in the direction of arrow 27. In order to make the connection, a universal adaptor 30 can be used that allows one to connect the plug portion 21 with the plug receiving portion 25. Universal adaptor 30 contains cylindrical plug receiving openings 31 that allows the insertion of cylindrical male prongs 22 of the plug portion 21. Rectangular male prongs 32 on the universal adaptor 30 can be inserted into rectangular female receptors 26 on the plug receiving portion 25 allowing the connection of the plug portion 21 through the universal adaptor 30 with the plug receiving portion 25. Universal adaptor 30 also contains triangular plug receiving openings 33 that would allow different electrodes/electrode pads from a different manufacturer to connect to the EKG and/or defibrillator machine.

Figure 3:
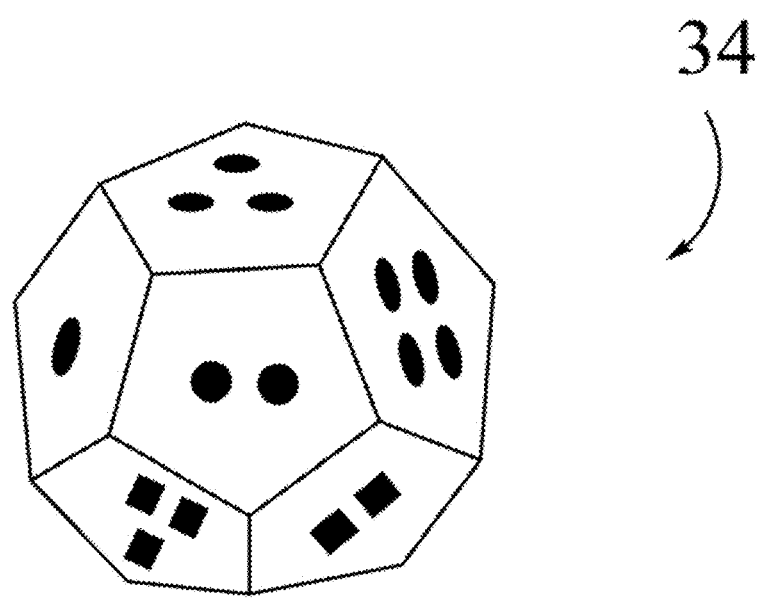
FIG. 3 shows a universal adaptor that has 12 faces on it.

It should be understood that the various male plugs and female receptors that are shown in FIG. 2 are for illustrative purposes only. The shapes/make-up of the male plugs and female receptors on the universal adaptor 30 will depend on the plugs and receptors that currently exist on presently available EKG/defibrillator machines. The universal adaptor 30 as shown is cubic in shape and thus could potentially have six different male plugs and/or female receptors associated with the universal adaptor, with each of the six different male plugs and/or female receptors present on each face of the cubic universal adaptor 30. It should be understood that any number of potential faces can be present on the universal, adaptor. It is contemplated that any number of faces can be present on the universal adaptor, for example a number of faces between 2 and 20 are contemplated and therefore within the scope of the invention. In FIG. 3, a universal adaptor 34 is shown that has 12 faces. It should be noted that each of the faces may have a different male plug or female receptor on it that allows any of a number of pads and EKGs/defibrillator to be connected to each other. In one embodiment, it is contemplated and therefore within the scope of the invention that the universal adaptor may not have a regular shape, as shown in for example FIG. 3, but may rather have an irregular shape such as the 12 faced shape of the universal adaptor shown in FIG. 3. In this embodiment, there may be a plurality of female receptors and or male plugs that allow a plurality of leads to be attached to the defibrillator EKG machine.

Figure 4:
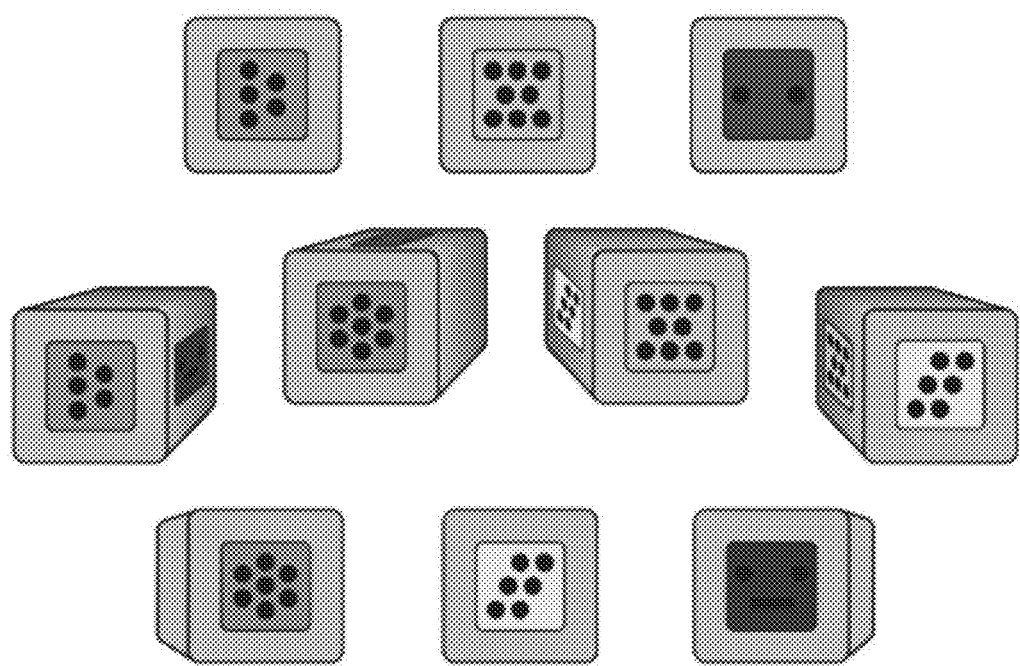
FIG. 4 shows various adaptors with six faces on them.

FIG. 4 shows a plurality of possible adaptors that all have six faces. It should be noted that all six faces may be occupied by female receptors and/or male plugs that will allow a plurality of different leads to be attached to different defibrillator/EKG machines from different manufacturers.

Although it is not shown, the inner components of a universal adaptor may contain any one or more of capacitors, operational amplifiers, resistors, diodes, or other electrical components that are necessary to adjust for differences in voltage, resistance, and/or current that may be present between the electrodes/electrode pads from one manufacturer and the EKG/defibrillator machine of a competitor. It should be noted that the universal adaptor may also be designed to be used in the cases where one manufacturer has a plurality of EKG and/or defibrillator machines that may have different lead, connections (from the electrodes/electrode pads to the EKG/defibrillator machines). Thus, the universal adaptor may be used to connect one line of a company's products (e.g., electrode pads) with a second line of a company's products (e.g., EKG machines) that may normally be incompatible.

In an embodiment of the invention, it is contemplated that more than one EKG and/or defibrillator machines may be connected to the universal adaptor allowing the more than one EKG and/or defibrillator machines to record heart patterns and/or to deliver requisite shocks. Thus, for example, an ambulances EKG and/or defibrillator may be attached to the same patient at the same time as a hospital's EKG and/or defibrillator machine. In an embodiment, the inner electronics in the universal adaptor are designed so that interference between different EKG and/or defibrillator machines is eliminated or at least minimized. In another embodiment, the inner electronics in the universal adaptor are designed so that one can "see" the results on one EKG machine that is connected to the universal adaptor of a shock that is delivered by a defibrillator machine that is also connected to the universal adaptor.

In an embodiment of the invention, it should be understood that by use of the universal adaptor, the time that it would normally take to switch out electrodes/electrode pads is now eliminated allowing a patient to receive faster lifesaving treatment. Thus, in an embodiment of the invention, the present invention relates to a method of saving lives that prior to the use of this universal adaptor was not previously known. It is contemplated that the use of the universal adaptor will save at least 10 minutes and up to 30 minutes relative to having to change electrodes/electrode pads that had to be done prior to the use of the use of the universal adaptor (when the EKG/defibrillator is from a different company than the company that makes the electrodes/electrode pads).

In an embodiment of the invention, the invention relates to a kit that comprises the elements that are necessary to connect a patient to an EKG machine such as electrodes, connecting wires, a universal adaptor, an amplifier, and a storage and transmission device. In an embodiment, the kit of the present invention comprises electrodes, or leads, that may be of two types, bipolar and/or unipolar electrodes. Bipolar limb leads may be used to record the voltage differential between the wrists and the legs. These electrodes can be placed on the left leg, the right wrist, and the left wrist, forming a triangular movement of the electrical impulse in the heart that can then be recorded. Unlike bipolar leads, unipolar leads record the voltage difference between a reference electrode and the body surface to which they are attached. These electrodes may be attached to the right and left arms and the right and left legs. Additionally, they may be placed at specific areas on the chest and are used to view the changing pattern of the heart's electrical activity.

In one embodiment, the universal adaptor is designed to be used with any of a plurality of different machines such as 3-lead, 5-lead, and 12-lead EKGs.

In an embodiment, the invention relates to an EKG and/or a defibrillator with a universal adaptor with a plurality of leads, wherein each lead views the heart from a different angle. The leads may be 3-lead or 5-lead EKGs, both of which are considered portable. The EKG may record limited heart activity, and are primarily used to monitor a patient's heart during surgery or on the way to the hospital in an ambulance.

In another embodiment the EKG may be a 12-lead machine that looks at the heart from twelve different angles and provides the type of readings necessary to diagnose and monitor patients with heart conditions of varying degrees. In a 12-lead EKG, six electrodes are attached to the skin on the chest around the heart. Four more electrodes are added, one on each arm and leg. The ten electrodes combine in twelve different ways to read twelve different angles on the heart. When the heart depolarizes with each heartbeat, the electrodes sense the tiny electrical impulses on the skin that are created as a result. The impulses travel back to the machine where they are interpreted and printed on a graph (either on screen and/or alternatively and/or additionally on paper).

Generally, each heart muscle cell has a negative charge at rest, but moves closer to a neutral charge with each beat, called depolarization. Each pair of electrodes records the changes in voltage created between the two when the heart depolarizes with each beat. A healthy heart will print out an orderly wave of progression with each heart beat, while a heart with diseased or damaged tissue will show certain irregularities in the heart's rhythm, size, or position, all of which can be measured by the present invention.

In one embodiment, the EKGs are fairly small in size and are considered portable and can be a part of a kit. The kit may comprise a small box that houses the machine, and a plurality of electrodes. In one embodiment, the impulses are picked up by the electrodes and are recorded in pairs, and each pair is known as a lead.

Accordingly, in an embodiment, the present invention relates to a universal adaptor that functions to connect electrodes and/or electrode pads from a first manufacturer to an EKG and/or defibrillator machine from a different second manufacturer. In a variation, the universal adaptor allows between 2 or 3 and 20 EKGs and/or defibrillators to be connected to the universal adaptor.

In an embodiment, the universal adaptor further comprises electrical components. The electrical, components may be one or more of capacitors, resistors, operational amplifiers, inductors, transistors, diodes, or mixtures thereof.

In an embodiment, the universal adaptor is made so as to accommodate different manufacturers' EKG and/or defibrillator accessories wherein the manufacturers are selected from the group consisting of Bionet, Brentwood Midmark, Burdick, Cardioline, Datex Ohmeda, Dr. Lee, Fukuda Denshi, General Electric, Hewlett Packard, Medtronic, Mortara, Nihon Kohden, Philips, QRS, Ritter, Schiller, Welch Allyn, Cardiac Science, Defibtech, HeartSine Technologies, Inc., Laerdal Medical Corporation. Medical Research Laboratories, Inc., Medtronic Physio-Control Corporation, Philips Medical Systems/Heartstream, Physio-Control, and ZOLL Medical Corporation.

In one embodiment, the universal adaptor may be part of a kit. The kit may further comprise at least one of electrodes, electrode adhering or non-adhering pads, a conductive gel, instructions, scissors, razor, gauze, cloth band-aids, plastic band-aids, first aid tape, alcohol, antiseptic wipes, hand sanitizer, gloves, blood pressure cuff stethoscope, scalpel, batteries, a battery charger, an AC/DC converter, an EKG machine or a defibrillator machine.

In one variation, the universal adaptor comprises at least one female receptors and at least one male prong. In a variation, the universal adaptor comprises a plurality of female receptors and male prongs. In one variation, the at least one female receptor on the universal adaptor connects to a lead that goes to electrodes or electrode pads on a patient, and the at least one male prong connects to a lead that goes to the EKG or defibrillator machine.

In an embodiment, the present invention relates to a kit that comprises a universal adaptor and at least one of electrodes, electrode adhering or non-adhering pads, a conductive gel, instructions, scissors, razor, gauze, cloth band-aids, plastic band-aids, first aid tape, alcohol, antiseptic wipes, hand sanitizer, gloves, blood pressure cuff, stethoscope, scalpel, batteries, a battery charger, an AC/DC converter, an EKG machine or a defibrillator machine.

In an embodiment, the present invention relates to a method of saving a patient's life that is undergoing a heart condition. In a variation, the present invention relates to a method of reducing the amount of time it takes to transfer a patient, undergoing a heart condition from ambulatory services to a hospital, said method employing the use of a universal adaptor that allows a plurality of different EKG and/or defibrillator machines to be connected to said patient. In one variation, the method allows electrodes and/or electrode pads that have been placed on said patient by the ambulatory services to remain on said patient when the different EKG and/or defibrillator machine is attached to said patient.

The method uses different EKG and/or defibrillator machines that are manufactured by a manufacturer selected from the group consisting of Bionet, Brentwood Midmark, Burdick, Cardioline, Datex Ohmeda, Dr. Lee, Fukuda Denshi, General Electric, Hewlett Packard, Medtronic, Mortara, Nihon Kohden, Philips, QRS, Ritter, Schiller, Welch Allyn, Cardiac Science, Defibtech, HeartSine Technologies, Inc., Laerdal Medical Corporation, Medical Research Laboratories, Inc., Medtronic Physio-Control Corporation, Philips Medical Systems/Heartstream, Physio-Control, and ZOLL Medical Corporation.

In an embodiment, the invention relates to a method that uses a universal adaptor that further comprises electrical components. In one variation, the electrical components comprise one or more of capacitors, resistors, operational amplifiers, inductors, transistors, diodes, or mixtures thereof. In one variation of the method, the universal adaptor comprises at least one female receptors and at least one male prong. Alternatively, in an embodiment of the method, the universal adaptor comprises a plurality of female receptors and male prongs. In a variation, the at least one female receptor on the universal adaptor connects to a lead that goes to electrodes or electrode pads on a patient, and the at least one male prong connects to a lead that goes to the EKG or defibrillator machine. In one variation, the method relates to an amount of time that it takes to transfer a patient that is reduced between about 10 minutes to about 30 minutes relative to a case wherein no universal adaptor is used.

It should be understood that the present invention is not to be limited by the above description. Modifications can be made to the above without departing from the spirit and scope of the invention. It is contemplated and therefore within the scope of the present invention that any feature that is described above can be combined with any other feature that is described above (even if those features are not described together). Moreover, it should be understood that the present invention contemplates and it is therefore within the scope of the invention that any element that is described can be omitted from the apparatus and/or methods of the present invention. In any event, the scope of protection to be afforded is to be determined by the claims which follow and the breadth of interpretation which the law allows.

I claim:

1. A universal adaptor that functions to connect electrode pads present on a patient wherein said electrode pads are from a first manufacturer to a defibrillator machine from a different second manufacturer wherein said electrode pads need not be removed from said patient and wherein said universal adaptor comprises a plurality of male prongs and a plurality of female receptors.

2. The universal adaptor of claim 1, wherein the universal adaptor allows between 3 and 20 defibrillators to be connected to the universal adaptor.

3. The universal adaptor of claim 1, further comprising electrical components.

4. The universal adaptor of claim 3, wherein electrical components comprise one or more of capacitors, resistors, operational amplifiers, inductors, transistors, diodes, or mixtures thereof.

5. The universal adaptor of claim 1, wherein a first manufacturer and a different second manufacturer is selected from the group consisting of Bionet, Brentwood Midmark, Burdick, Cardioline, Datex Ohmeda, Dr. Lee, Fukuda Denshi, General Electric, Hewlett Packard, Medtronic, Mortara, Nihon Kohden, Philips, QRS, Ritter, Schiller, Welch Allyn, Cardiac Science, Defibtech, HeartSine Technologies, Inc., Laerdal Medical Corporation, Medical Research Laboratories, Inc., Medtronic Physio-Control Corporation, Philips Medical Systems/Heartstream, Physio-Control, and ZOLL Medical Corporation.

6. The universal adaptor of claim 1, wherein the universal adaptor is part of a kit.

7. The universal adaptor of claim 6, wherein the kit further comprises at least one of electrodes, electrode adhering or non-adhering pads, a conductive gel, instructions, scissors, razor, gauze, cloth band-aids, plastic band-aids, first aid tape, alcohol, antiseptic wipes, hand sanitizer, gloves, blood pressure cuff, stethoscope, scalpel, batteries, a battery charger, an AC/DC converter, an EKG machine or a defibrillator machine.

8. The universal adaptor of claim 1, wherein the universal adaptor comprises twelve faces.

9. The universal adaptor of claim 8, wherein at least one female receptor on the universal adaptor connects to a lead that goes to electrode pads on a patient, and at least one male prong connects to a lead that goes to the defibrillator machine.

10. The universal adaptor of claim 1, wherein the universal adaptor comprises 6 faces.

11. A kit that comprises a universal adaptor for a defibrillator to connect electrode pads from one manufacturer to a defibrillator from a different second manufacturer, and at least one of electrodes, electrode adhering or non-adhering pads, a conductive gel, instructions, scissors, razor, gauze, cloth band-aids, plastic band-aids, first aid tape, alcohol, antiseptic wipes, hand sanitizer, gloves, blood pressure cuff, stethoscope, scalpel, batteries, a battery charger, an AC/DC converter, or a defibrillator machine wherein said universal adaptor comprises a plurality of male prongs and a plurality of female receptors.

12. The kit of claim 11, wherein the universal adaptor comprises 6 faces.

13. A method of reducing the amount of time it takes to transfer a patient undergoing a heart condition from ambulatory services to a hospital, said method employing the use of a universal adaptor that allows a plurality of different defibrillator machines to be connected to said patient, wherein said different defibrillator machines can be connected via said universal adaptor without removing electrode pads from said patient and wherein said universal adaptor comprises a plurality of male prongs and a plurality of female receptors.

14. The method of claim 13, wherein said method allows electrodes and/or electrode pads that have been placed on said patient by the ambulatory services to remain on said patient when the different defibrillator machine is attached to said patient.

15. The method of claim 14, wherein said different defibrillator machine is manufactured by a manufacturer selected from the group consisting of Bionet, Brentwood Midmark, Burdick, Cardioline, Datex Ohmeda, Dr. Lee, Fukuda Denshi, General Electric, Hewlett Packard, Medtronic, Mortara, Nihon Kohden, Philips, QRS, Ritter, Schiller, Welch Allyn, Cardiac Science, Defibtech, HeartSine Technologies, Inc., Laerdal Medical Corporation, Medical Research Laboratories, Inc., Medtronic Physio-Control Corporation, Philips Medical Systems/Heartstream, Physio-Control, and ZOLL Medical Corporation.

16. The method of claim 13, wherein the universal adaptor further comprises electrical components.

17. The method of claim 16, wherein electrical components comprise one or more of capacitors, resistors, operational amplifiers, inductors, transistors, diodes, or mixtures thereof.

18. The method of claim 16, wherein the universal adaptor comprises twelve faces.

19. The method of claim 18, wherein at least one female receptor on the universal adaptor connects to a lead that goes to electrode pads on a patient, and at least one male prong connects to a lead that goes to the defibrillator machine.

20. The method of claim 13, wherein the amount of time it takes to transfer a patient is reduced between about 10 minutes to about 30 minutes relative to a case wherein no universal adaptor is used.

* * * * *